United States Patent [19]

Jung et al.

[11] Patent Number: 5,942,503
[45] Date of Patent: Aug. 24, 1999

[54] USE OF EPINASTINE FOR THE TREATMENT OF PAIN

[75] Inventors: Birgit Jung, Schwabenheim; Christopher John Montague Meade, Bingen; Michel Pairet, Biberach, all of Germany

[73] Assignee: Boehringer Indelheim KG, Ingelhiem, Germany

[21] Appl. No.: 09/066,392

[22] PCT Filed: Nov. 13, 1996

[86] PCT No.: PCT/EP96/04957

§ 371 Date: Jun. 9, 1998

§ 102(e) Date: Jun. 9, 1998

[87] PCT Pub. No.: WO97/17971

PCT Pub. Date: May 22, 1997

[30] Foreign Application Priority Data

Nov. 14, 1995 [DE] Germany .......... 195 42 281.3

[51] Int. Cl.$^6$ ........................ A61K 31/55
[52] U.S. Cl. ........................ 514/214
[58] Field of Search ................ 514/214, 213, 514/212

[56] References Cited

PUBLICATIONS

Jackson et al, Clin. Exp. Pharmacol. Physiol., vol. 19, No. 1, pp. 17–23, 1992.

*Primary Examiner*—William R. A. Jarvis
*Attorney, Agent, or Firm*—R. P. Raymond; M-E. M. Devlin; A. R. Stempel

[57] ABSTRACT

Disclosed herein is the use of epinastine for the treatment of pain, including migraine, Bing-Horton syndrome, tension headaches, muscle pain, inflammatory pain, and neuralgias. Epinastine may also be administered in combination with an additional analgesic for treating pain.

11 Claims, No Drawings

USE OF EPINASTINE FOR THE TREATMENT OF PAIN

This application is a 371 of PCT/EP96/04957, filed Nov. 13, 1996.

The present invention relates to a new use of epinastine for the treatment and prophylaxis of pain, especially chronic or inflammation-induced pain and in particular migraine.

Epinastine (3-amino-9,13b-dihydro-1H-dibenz[c,f]-imidazo[5,1-a]azepine hydrochloride) was described by Fügner et al. [Arzneimittelforschung 38 (1988): 1446–1453]. The active principle can be used in the form of a racemate or in the form of pure enantiomers or as a mixture of different proportions of both enantiomers. Therapeutically, epinastine is used as the hydrochloride. The invention described herein, however, is not limited to the hydrochloride but relates to any addition salt with a pharmacologically acceptable acid as well as the free base.

The use of epinastine and its salts for the treatment of asthma is known. European patent EP-B-0 035 749 discloses that this substance is also suitable for therapy of allergic diseases such as allergic rhinitis, allergic conjunctivitis and allergic bronchitis.

Headache is a commonly occurring symptom. In most cases the headache is of short duration and can readily be controlled by weak analgesics such as aspirin, paracetamol or ibuprofen. Such headache is bothersome but does not lead to any significant impairment of health. By contrast, chronic recurring headaches such as migraine can lead to such serious adverse affects that a doctor has to be consulted. These serious types of headaches often cannot be treated satisfactorily with a weak analgesic.

On the other hand, there is no universally accepted system of classifying headache; chronic recurring pain in the sense of this invention refers predominantly to migraine and Bing-Horton syndrome. Migraine itself incorporates several sub-forms [see J. Olesen and R. B. Lipton, Neurology 44 (1994) p6–p10 for a classification]. Although migraine and tension headaches are two different forms, several scientists see them as a clinical continuum with migraine at one end and tension headache at the other other end of the spectrum [K. L. Kumar and T. G. Cooney: "Headaches" in "Medical Clinics of North America" Vol. 79 No. 2 (1995) p.261 to 286]. Therefore it seems reasonable to suppose that many patients with tension headache will also respond to a therapy for migraine. Several other diseases which are associated with chronic pain, such as neuralgia, muscle pains and inflammation pain (as for example after sunburn or in osteoarthritis or after sports injuries) have common features with chronic recurring pain [A. Dray, L. Urban and A. Dickenson, Trends in Pharmacological Sciences 15 (1994): 190–197].

Existing therapy for migraine includes the use of ergot alkaloids such as ergotamine and $5HT_{1D}$ agonists such as sumatriptan. Although many patients profit from these medicaments, by no means all patients respond. Further, there are numerous side effects such as dizziness and nausea. Drugs for prophylactic management of migraine include methysergide and pizotifen, beta-blockers such as propanolol, and calcium channel blockers such as flunarizine. Chronic administration of these drugs can have side effects that impair the patients' quality of life and the drugs usually only reduce the frequency of migraine attacks but do not abolish them [see H. C. Diener, Eur. Neurol. 34(Suppl 2) (1994): 18–25.]

There therefore remains a need to provide a drug for the treatment of migraine which is not only effective but also free of significant side effects. There is also a need to provide a medicament with a high degree of safety for particular patient groups such as children, and patients with reduced liver or kidney function, or cardiovascular disease.

It has now been found that, surprisingly, epinastine fulfils these requirements to an exceptional degree. This is shown by the following research results:

In laboratory animals, it is possible to induce inflammation in the dura mater by electrical stimulation of the trigeminal ganglion, which causes the release of neuropeptides such as substance P from sensory nerve endings. Plasma extravasation can be monitored by markers such as Evans blue. This animal model is widely used for testing for drugs useful in migraine. Surprisingly, epinastine shows exceptionally good activity in this model. For chronic inflammatory pain, a widely used animal model is that first described in principle by Randall and Selitto (L. O. Randall, and J. J. Selitto, Arch. Int. Pharmacodyn. 111 (1957): 409–419). Inflammation is induced in the paw of a rat by injection of yeast cells and the inflammation-induced hyperalgesia measured. Epinastine also showed surprisingly good activity in this model.

Epinastine is known as an antihistamine. The interaction between a ligand (e.g. a drug) and a receptor can be quantified by means of an affinity constant ($K_i$). The smaller the value of the affinity constant, so the stronger is the binding between drug and receptor. Especial attention is paid to those compounds which show a $K_i$ value that is smaller or in the same order of magnitude as the expected concentration of drug in target tissues (or plasma). The $5HT_7$ receptor is a special subtype of 5-hydroxytryptamine binding receptor (for a classification see 'Trends in Pharmacological Sciences 1994 Receptor & Ion Channel Nomenclature Supplement'). Surprisingly, a good binding of epinastine to the $5HT_7$ receptor has been found. The $K_i$ values for epinastine and two comparison antihistamines are listed in Table 1.

The invention described herein will now be illustrated with reference to Examples. Other possibilities will be apparent to one skilled in the art from this description. It is specifically pointed out that the examples are intended only to illustrate and not to limit the present invention.

EXAMPLES

Study of binding of epinastine of the $5HT_7$ receptor.

Binding of 2.0 nM [$^3$H] LSD to a rat $5HT_7$ receptor expressed in CHO cells was measured for 60 minutes at 37° C. in 50 mM Tris-HCl buffer, pH 7.4, containing 10 mM $MgCl_2$ and 0.5 mM EDTA. The reaction was terminated by rapid vacuum filtration onto glass fiber filters pretreated with 0.1% polyethyleneimine. Binding studies were made in duplicate in the absence of the drug and in the presence of between 6 and 8 concentrations of epinastine between 3 nM and 10 $\mu$M. Radioactivity trapped on the filters in the presence of each drug concentration was measured and compared with control values in order to ascertain interaction of the drug with the cloned 5-$HT_7$ receptor site. Non-specific binding was determined in the presence of 5-carboxamidotryptamine (5-CT). The $IC_{50}$ for the displacement of radiolabelled ligand was determined by graphical extrapolation and $K_i$ values were calculated after correction for the radioligand occupancy shift by the Cheng and Prusoff equation (see Biochem. Pharmacol. 22, (1973): 3099–3108). Three experiments were carried out. In each experiment epinastine was found to bind the $5HT_7$ receptor surprisingly well. The mean $K_i$ value for epinastine found was 33 nM, the mean $K_i$ of the (+) enantiomer was 28 nM, and of the (−) enantiomer 189 nM. The individual values for the $K_i$ of epinastine and its enantiomers which were found in the three experiments carried out are listed in table 1, together with $K_i$ values for two comparison antihistamines:

TABLE 1

Binding of Epinastine (Racemate and Enantiomers) and two comparison antihistamines (ketotifen and mepyramine) to the $5HT_7$ receptor

| Compound | Full chemical name | Measured $K_i$ values, nM |
|---|---|---|
| Epinastine | 3-Amino-9,13b-dihydro-1H-dibenz-[c,f]-imidazo[1,5a]azepine-hydrochloride (racemate) | 27, 41, 30 |
| Epinastine (+) Enantiomer | (+)-3-Amino-9,13b-dihydro-1H-dibenz-[c,f]-imidazo[1,5a]-azepine-hydrochloride | 45, 18, 22 |
| Epinastine (−) Enantiomer | (−)-3-Amino-9,13b-dihydro-1H-dibenz-[c,f]-imidazo[1,5a]-azepine-hydrochloride | 155, 204, 207 |
| Ketotifen | | 406, 572, 331 |
| Mepyramine | | 2660, 747, 1330 |

Study of the Effect of Epinastine on the Plasma Extravasation in the Dura Mater of Rats Induced by Electrical Stimulation of the Trigeminal Ganglion Male Wistar rats weighing 175–190 g were anaesthetised with nembutal 50 mg/kg i.p. and the jugular vein was cannulated for injection of drugs. The animals were placed in a stereotaxic frame. Symmetrical boreholes were drilled 3.0 mm laterally and 3.2 mm posteriorly from bregma and the electrodes were lowered 9.5 mm from dura mater. The test compound epinastine or control solution were administered intravenously 10 min prior to electrical stimulation of the right trigeminal ganglion (5 min; 2.0 mA, 5 Hz, 5 ms duration and Evans blue (30 mg/kg i.v.), was given 5 min prior to electrical stimulation as a marker of plasma protein extravasation. 15 minutes after the end of the stimulation period the animals were perfused with 50 ml saline via the left cardiac ventricle to remove intravascular Evans blue. The dura mater was removed, blotted dry and weighed. Tissue Evans blue was extracted in 0.3 ml formamide at 50° C. for 24 h. Dye concentrations were measured with a spectrophotometer at 620 nm wavelength, interpolated on a standard curve and expressed as ng Evans blue content per mg tissue weight.

Calculation of Data:

Extravasation was expressed as the quotient calculated by dividing the Evan's blue content of the stimulated side by the Evan's blue content of the unstimulated side. Results are expressed as means. The results are listed in Table 2.

TABLE 2

| animal number | body weight | Dura mater of stimulated side | | | Dura mater of non-stimulated side | | | Quotient stimulated/ non-stimulated side |
|---|---|---|---|---|---|---|---|---|
| | | wet weight [mg] | EB-content [µg/ml] | EB/wet weight [µg/mg] | wet weight [mg] | EB-content [µg/ml] | EB/wet weight [µg/mg] | |
| Effect of epinastine in an animal model of migraine Control group treated with 0.9% sodium chloride solution: 1 ml/kg i.v. | | | | | | | | |
| 1 | 180 g | 4.24 | 0.85 | 0.060 | 5.58 | 0.73 | 0.039 | 1.54 |
| 2 | 185 g | 5.34 | 0.76 | 0.043 | 5.13 | 0.60 | 0.035 | 1.23 |
| 3 | 185 g | 5.06 | 0.47 | 0.028 | 4.60 | 0.38 | 0.025 | 1.12 |
| 4 | 190 g | 6.05 | 1.33 | 0.066 | 6.23 | 1.03 | 0.050 | 1.32 |
| 5 | 185 g | 4.22 | 0.72 | 0.051 | 5.77 | 0.67 | 0.035 | 1.46 |
| 6 | 185 g | 4.81 | 0.57 | 0.036 | 5.03 | 0.54 | 0.032 | 1.13 |
| 7 | 185 g | 7.62 | 1.35 | 0.053 | 6.53 | 1.22 | 0.056 | 0.95 |
| | | | | | | | mean | 1.25 |
| Group treated with epinastine 10 µg/kg i.v. dissolved in 0.9% sodium chloride solution: 1 ml/kg | | | | | | | | |
| 1 | 175 g | 6.63 | 1.20 | 0.054 | 6.01 | 1.28 | 0.064 | 0.84 |
| 2 | 175 g | 4.96 | 0.74 | 0.046 | 4.78 | 0.80 | 0.050 | 0.92 |
| 3 | 170 g | 4.63 | 0.53 | 0.034 | 7.68 | 1.01 | 0.039 | 0.87 |
| 4 | 165 g | 6.52 | 0.54 | 0.025 | 6.29 | 0.53 | 0.025 | 1.00 |
| 5 | 190 g | 7.97 | 1.23 | 0.046 | 9.32 | 1.39 | 0.045 | 1.02 |
| 6 | 190 g | 6.24 | 0.70 | 0.034 | 6.52 | 0.83 | 0.038 | 0.89 |
| 7 | 190 g | 6.87 | 0.60 | 0.026 | 7.29 | 0.48 | 0.020 | 1.30 |
| | | | | | | | mean | 0.98 |

EB = Evans blue

Table 2 shows that in the animal model for migraine the treatment with epinastine significantly reduced the Evans blue extravasation induced by electrical stimulation of the trigeminal ganglion.

Study of the Effect of Epinastine on Yeast-Induced Hyperalgesia in the Rat Paw The method of Randall and Selitto was modified through use of the Analgesia meter by Basile of Milan.

Groups of 10 fasted rats of the strain Chbb:THOM (weight 110–140 g, 5 male 5 female) were dosed orally with it Natrosol 250 HX, 1 ml/100 g body weight, containing 0, 0.3, 1.0, 3.0 or 10 mg/kg epinastine (racemic mixture). 1 hour later the rats were injected subplantar with a suspension of yeast cells in a volume 0.1 ml into the right hind paw. 3 hours after injection of the yeast suspension, the pain threshold was determined by increasing the pressure on the inflamed paw until a sign of pain was produced. From the pain threshold measured after the different doses of the epinastine, linear regression analysis was used to determine an $ED_{50}$. As Table 3 shows, epinastine increased the pain threshold in this model. The dose of epinastine required to increase the pain threshold by 50% was calculated as 1.1 mg/kg.

TABLE 3

Effect of epinastine on pain threshold in inflamed rat paw.

| Substance | Dose mg/kg p.o. | Number of rats | Mean value of pain threshold g/hind paw | Standard deviation | % Increase |
|---|---|---|---|---|---|
| Control | 0.0 | 10 | 150.4 | 30.4 | |
| Epinastine | 0.3 | 10 | 164.8 | 41.8 | 9.6 |
| Epinastine | 1.0 | 10 | 235.2 | 51.5 | 56.4 |
| Epinastine | 3.0 | 10 | 259.4 | 60.7 | 72.5 |
| Epinastine | 10.0 | 10 | 272.8 | 60.9 | 81.4 |

TABLE 4

Test of analgesic activity according to Randall Selitto

| Animal: | male/female rat |
|---|---|
| Weight: | 110 to 140 g |
| Feeding: | Fasting |
| Administration: | 1.0 ml/100 g p.o. |
| Excipient: | 1% Natrosol |
| 90 minute value | |

| Substance | Dose mg/kg | N | Mean value | Activity in % | SD | VK in % |
|---|---|---|---|---|---|---|
| Control | 0/0 | 10 | 150 | | 46.188 | 30.792 |
| Epinastine/ ibuprofen | 0/3.0 | 10 | 153 | 2.00 | 20.028 | 13.090 |
| Epinastine/ ibuprofen | 0/10.0 | 10 | 202.00 | 34.67 | 29.740 | 14.723 |
| Epinastine/ ibuprofen | 0.3/0 | 10 | 216.00 | 44.00 | 44.020 | 20.380 |
| Epinastine/ ibuprofen | 0.3/3.0 | 10 | 252.00 | 68.00 | 57.116 | 22.665 |
| Epinastine/ ibuprofen | 0.3/10.0 | 10 | 277.00 | 84.67 | 81.792 | 29.528 |
| Epinastine/ ibuprofen | 1.0/0 | 10 | 232.00 | 54.67 | 57.889 | 24.952 |
| Epinastine/ ibuprofen | 1.0/3.0 | 10 | 295.00 | 96.67 | 70.593 | 23.930 |
| Epinastine/ ibuprofen | 1.0/10.0 | 10 | 369.00 | 146.00 | 107.233 | 29.060 |

Epinastine or its enantiomers may be given for the treatment of pain as an aqueous solution for injection by a suitable route such as intravenous, intramuscular or subcutaneous, as a tablet, as a suppository, as a cream, as a plaster for transdermal application, as an aerosol for inhalative administration to the lung, or as a nasal spray.

When dosed as a tablet or suppository the single dose for adults lies between 5 and 200 mg, with the preferred dose between 10 and 50 mg. For inhalation single doses between 0.05 and 20 mg, preferably between 0.2 and 5 mg are administered. For parenteral injection the single dose lies between 0.1 and 50 mg with a preferred dose between 0.5 and 20 mg. The cited doses may if necessary be given several times in a day.

Particularly preferred and advantageous appears to be the combination of epinastine with other therapeutic agents, for example aspirin, paracetamol, non-steroidal anti-inflammatory drugs (NSAID) such as ibuprofen, meloxicam, indomethacin or naproxen; $5HT_{1D}$ agonists such as sumatriptan, MK-462, naratriptan or 311C; CP-122, 288; UK 116,044; dopamine $D_2$ receptor antagonists such as metoclopramide; ergot alkaloids such as ergotamine, dihydroergotamine or metergoline; clonidine; methysergide; dotarizine; lisuride; pizotifen; valproic acid; aminotryptiline; beta blockers such as propanolol or metoprolol; calcium channel antagonists such as flunarizine or lomerizine, or neurokinin antagonists. Such a combination, either in a single dosage form or in separate forms able to be administered sequentially or substantially simultaneously, comprises a further feature of the invention.

The following are examples of pharmaceutical formulations containing the active principle:

Tablets:
  Epinastine 20 mg
  Magnesium stearate 1 mg
  Maize starch 62 mg
  Lactose 83 mg
  Polyvinylpyrrolidone 1.6 mg Injectable solution:
  Epinastine 0.3 g
  Sodium chloride 0.9 g
  Water for injection to 100 ml.

The solution may be sterilised using standard methods.

Solution for nasal or inhalative administration:
  Epinastine 0.3 g
  Sodium chloride 0.9 g
  Benzalkonium chloride 0.01 mg
  Purified water to 100 ml.

The solution described above is suitable for nasal administration as a spray, or in combination with a device which is able to produce an aerosol of particle size with preferred size distribution 2 to 6 $\mu M$, for administration to the lung.

Capsules for inhalation:
  Epinastine is applied in a micronised form (particle size between 2 and 6 $\mu M$) usually with addition of micronised carrier substance such as lactose and filled into a capsule of hard gelatin. For inhalation, the usual devices for administering powders to the lung can be applied. Each capsule contains between 0.2 and 20 mg epinastine and 0 and 40 mg lactose.

Inhalation aerosol
  Epinastine 1 part
  Soya lecithin 0.2 parts
  Propellant gas mixture to 100 parts.

The mixture is preferably filled into an aerosol canister with a metering valve, the individual puff being so measured that a dose of 0.5 mg is administered. For other doses in the suggested dose ranges the appropriate preparation with a larger or smaller amount of active principle is used.

| Cream | |
|---|---|
| Composition | g/100 g cream |
| Epinastine | 2 |
| Concentrated hydrochloric acid | 0.011 |
| Sodium pyrosulphite | 0.050 |
| Mixture of equal parts of cetyl alcohol and stearyl alcohol | 20 |
| White vaseline | 5 |
| Synthetic bergamot oil | 0.075 |
| Distilled water to | 100 |

The components are mixed in the usual way for preparation of a cream.

what is claimed is:

1. A method for treating pain in a patient in need thereof which comprises administering to said patient an analgesia producing amount of epinastine or a pharmaceutically acceptable salt thereof.

2. A method for treating migraine, Bing-Horton syndrome, tension headache, muscular pain, inflammatory pain or neuralgias in a patient in need thereof which comprises administering to said patient an analgesia-producing amount of epinastine or a pharmaceutically acceptable salt thereof.

3. A method for treating pain in a patient in need thereof which comprises administering to said patient an analgesia producing amount of epinastine, or a pharmaceutically acceptable salt thereof, in combination with another analgesia-producing agent.

4. The method of claim 3 wherein the further analgesic used is an NSAID, a $5HT_{1D}$-agonist, a dopamine $D_2$ receptor antagonist, an ergot alkaloid, a beta blocker, a calcium channel blocker or a neurokinin antagonist.

5. The method according to claim 4, in which the NSAID is ibuprofen, meloxicam, indomethacin or naproxen.

6. The method according to claim 4, in which the $5HT_{1D}$ agonist is sumatriptan, MK-462, naratriptan or 311C.

7. The method according to claim 4, in which the dopamine $D_2$ receptor antagonist is metoclopramide.

8. The method according to claim 4, in which the ergot alkaloid is ergotamine, dihydroergotamine or metergoline.

9. The method according to claim 4, in which the beta-blocker is propoanolol or metoprolol.

10. The method according to claim 4, in which the calcium channel blocker is flunarizine or lomerizine.

11. The method according to claim 3, in which the analgesia-producing agent that is combined is aspirin, paracetamol, clonidine, methysergide, dotarizine, lisuride, pizotifen, valproic acid, aminotryptiline, CP-122,288 or UK 116,044.

* * * * *